(12) United States Patent
Javet et al.

(10) Patent No.: US 7,018,426 B2
(45) Date of Patent: Mar. 28, 2006

(54) OXIDATION DYE

(75) Inventors: Manuela Javet, Marly (CH); Christel Dousse, Courtepin (CH)

(73) Assignee: Wella AG, Darmstadt (DE)

( * ) Notice: Subject to any disclaimer, the term of this patent is extended or adjusted under 35 U.S.C. 154(b) by 224 days.

(21) Appl. No.: 10/240,587

(22) PCT Filed: Sep. 13, 2001

(86) PCT No.: PCT/EP01/10587

§ 371 (c)(1),
(2), (4) Date: Oct. 2, 2002

(87) PCT Pub. No.: WO02/069919

PCT Pub. Date: Sep. 12, 2002

(65) Prior Publication Data

US 2003/0159222 A1   Aug. 28, 2003

(30) Foreign Application Priority Data

Mar. 1, 2001 (DE) .............................. 101 09 805

(51) Int. Cl.
*A61K 7/13* (2006.01)
(52) U.S. Cl. ................... 8/405; 8/406; 8/407; 8/408; 8/409; 8/424; 8/570; 8/573; 8/688; 8/690; 8/670; 548/302.7
(58) Field of Classification Search ............ 8/405, 8/406, 408, 409, 424, 570, 573, 688, 690, 8/670; 548/302.7
See application file for complete search history.

(56) References Cited

U.S. PATENT DOCUMENTS

| | | | | |
|---|---|---|---|---|
| 5,061,289 A | * | 10/1991 | Clausen et al. ............... | 8/405 |
| 5,540,738 A | * | 7/1996 | Chan et al. .................. | 8/406 |
| 5,663,366 A | | 9/1997 | Neunhoeffer et al. ...... | 548/371.4 |
| 6,074,438 A | * | 6/2000 | Lim et al. .................... | 8/409 |

FOREIGN PATENT DOCUMENTS

| | | |
|---|---|---|
| DE | 42 34 885 A1 | 4/1994 |
| DE | 42 34 887 A1 | 4/1994 |
| DE | 196 43 059 A | 4/1998 |
| DE | 197 30 412 C1 | 12/1998 |
| DE | 200 13 156 U | 10/2000 |
| DE | 199 51 010 A | 4/2001 |
| DE | 199 59 318 A | 6/2001 |
| EP | 0 375 977 A1 | 7/1990 |
| EP | 0 740 931 A1 | 11/1996 |

\* cited by examiner

*Primary Examiner*—Eisa Elhilo
(74) *Attorney, Agent, or Firm*—Michael J. Striker

(57) ABSTRACT

The object of the invention is an agent for the oxidative dyeing keratin fibers, wherein it contains (a) at least one 4,5-diaminopyrazole derivative of Formulas (I), (II) or (III) or its salt with organic or inorganic acids

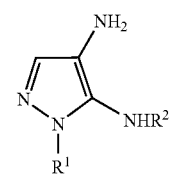

(I)

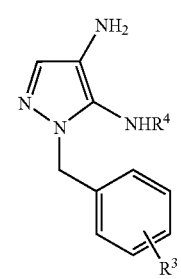

(II)

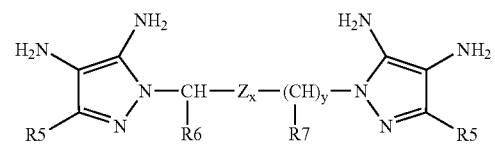

(III)

as well as
(b) at least one resorcinol derivative of the general Formula (IV)

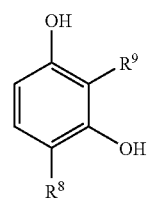

(IV)

9 Claims, No Drawings

OXIDATION DYE

The object of the present invention are agents for oxidatively dyeing keratin fibers, particularly human hair, which contain certain diaminopyrazole derivatives as developing substance and certain resorcinol derivatives as coupler substance.

Hair dyeing agents are divided mainly into oxidation dyeing agents and non-oxidative tinting, depending on the starting color of the hair, which is to be dyed, and on the desired end result. At the present time, oxidative hair dyes have attained a significant importance. The dyeing is brought about here by the reaction of certain developer substances with certain coupler substances in the presence of suitable oxidizing agents.

Oxidation dyes, which are used to dye human hair, must fulfill numerous requirements. They must be physiologically compatible and provide dyeings in the desired intensity. In addition, the hair dyeings should be highly resistant against the effects of light, permanent waving agents and acids, as well as friction, and remain stable for at least 4 to 6 weeks under normal conditions.

In addition, an oxidative dyeing system must make possible a wide range of different color nuances in the range of natural shades as well as of fashion shades. This means that, on the one hand, yellow, red and blue dyes must be possible for the fashion shade range and, on the other, blond, brown and black dyes for the natural shade range. The natural shades can also be obtained by mixing different dyes, which produce yellow, red and blue.

As developer substances in the fashion shade range, 4,5-diamino-pyrazole derivatives, which are tolerated well physiologically, have gained acceptance recently. They produce very intensive red, violet and blue color shades with different coupler compounds. Such oxidation dyeing agents, which contain pyrazoles, are described, for example, in the DE-OS 42 34 885, DE-OS 42 34 887, DE-PS 197 30 412, EP-OS 0 375 977 and EP-OS 0 740 931.

Brilliant color nuances in the orange and red ranges are produced, above all, with 4,5-diaminopyrazole derivatives as developers and 3-aminophenols, particularly 6-alkyl-3-aminophenols as couplers. However, the dyeings have the disadvantage that, in some cases, they "bleed" excessively. This can lead to unpleasant discolorations on clothing and pillows, when the hair becomes moist, for example, due to perspiration or rain.

It is therefore an object of the present invention to make available a system of developer and coupler substances, which is suitable for the orange and red color ranges and contains certain diaminopyrazole derivatives as developer substance and shows practically no bleeding even when subjected to the action of moisture.

It has now been discovered that this objective can be accomplished by the use of certain resorcinol derivatives as coupler substance. The object of the present invention therefore is an agent for the oxidative dyeing of keratin fibers, especially of human hair, wherein the agent contains (a) at least one 4,5-diaminopyrazole derivative of Formulas (I), (II) or (III) or its salt with organic or inorganic acids,

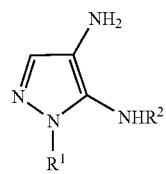
(I)

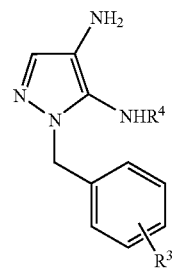
(II)

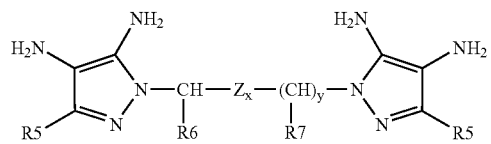
(III)

wherein R1 and R2 independently of one another represent hydrogen, a linear or branched $C_1$–$C_6$ alkyl group, an optionally substituted phenyl group or a linear or branched $C_2$–$C_4$-hydroxyalkyl group;

R3 represents a halogen atom (F, Cl, Br, I), a linear or branched $C_1$–$C_4$ alkyl group or a linear or branched $C_1$–$C_4$ alkoxy group and R4 represents hydrogen, a linear or branched $C_1$–$C_4$ alkyl group or a linear or branched $C_2$–$C_4$ hydroxy alkyl group;

R5 represents hydrogen, a linear or branched $C_1$–$C_6$ alkyl group, a $C_1$–$C_4$ hydroxy alkyl group, a $C_1$–$C_4$ aminoalkyl group, a $C_1$–$C_8$ alkylamino group, a di($C_1$–$C_8$) alkylamino group, a $C_1$–$C_4$ alkylamino-($C_1$–$C_4$)alkyl group or a di($C_1$–$C_4$) alkylamino-($C_1$–$C_4$) alkyl group, an aryl group or a heteroaryl group;

R6 and R7 may be identical or different and represent hydrogen, a linear or branched $C_1$–$C_6$ alkyl group, an aryl group, a heteroaryl group, a carboxylic acid group, a carboxylic ester group, an unsubstituted or substituted carboxylic acid amide group, a hydroxy group or a $C_1$–$C_4$ hydroxyalkyl group or R2 and R3 jointly form an optionally substituted $C_1$–$C_6$ alkylene group;

Z is a $C_1$–$C_{10}$ alkyl diradical, which is optionally interrupted by a hetero atom (such as a nitrogen, oxygen or sulfur atom), an aromatic or heteroaromatic diradical, which is optionally condensed with one or two benzene rings and/or substituted by a hydroxy group or a $C_1$–$C_6$ alkyl group, or a diradical of formula —Ar(Alk)$_n$—Ar—, in which Ar is an optionally substituted aryl or heteroaryl group, especially a phenylene or pyridyl group, Alk is a —CH$_2$ group and n is a whole number from 0 to 6; and x and y independently of one another are equal to 0 or 1;

and (b) -at least one resorcinol derivative, which is substituted in 4 position, and has the general formula (IV)

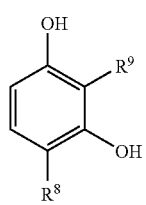
(IV)

wherein
R8 is a linear or branched $C_1$–$C_8$ alkyl group, a linear or branched $C_1$–$C_8$ hydroxyalkyl group, a linear or branched $C_1$–$C_4$ alkoxy-$C_1$–$C_8$ alkyl group or a linear or branched $C_1$–$C_8$ aminoalkyl group; and R9 is hydrogen, a linear or branched $C_1$–$C_8$ alkyl group, a linear or branched $C_1$–$C_8$ hydroxyalkyl group, a linear or branched $C_1$–$C_4$ alkoxy-$C_1$–$C_8$ alkyl group or a linear or branched $C_1$–$C_8$ aminoalkyl group.

In particular, the following may be mentioned as preferred 4,5-diaminopyrazole derivatives of Formulas (I), (II) and (III): 4,5-diamino-1-methyl-1H-pyrazole; 4,5-diamino-1-(4'-methylbenzyl)-pyrazole; 4,5-diamino-1-(3'-methylbenzyl)-pyrazole; 4,5-diamino-1-(2'-methylbenzyl)-pyrazole; 4,5-diamino-1-(2'-hydroxyethyl)-1H-pyrazole; 4,5-diamino-1-benzyl-1H-pyrazole; 4,5-diamino-1-ethyl-1H-pyrazole; 4,5-diamino-1-isopropyl-1H-pyrazole; 4,5-diamino-1-pentyl-1H-pyrazole; 4,5-diamino-1-(4'-methoxybenzyl)-1H-pyrazole; 4,5-diamino-1H-pyrazole; 4,5-diamino-1-(3'-methoxybenzyl)-1H-pyrazole; 4,5-diamino-1-(2'-methoxybenzyl)-1H-pyrazole; 4,5-diamino-1-(4'-chlorobenzyl)-1H-pyrazole; 4,5-diamino-1-(3'-chlorobenzyl)-1H-pyrazole; 4,5-diamino-1-(2'-chlorobenzyl)-1H-pyrazole; 4-amino-5-methylamino-1-(4'-methoxybenzyl)-1H-pyrazole; 4-amino-5-(2'-hydroxyethyl)amino-1-(4'-methoxybenzyl)-1H-pyrazole; 4-amino-5-methylamino-1-(2'-hydroxyethyl)-1H-pyrazole; bis-(4,5-diamino-pyrazole-1-yl)-methane; 1,2-bis-(4,5-diamino-pyrazole-1-yl)-ethane; 1,3-bis-(4,5-diamino-pyrazole-1-yl)-propane; 1,3-bis-(4,5-diamino-3-phenyl-pyrazole-1-yl)-propane; 2,3-bis-(4,5-diamino-pyrazole-1-yl)-propane-1-ol; N-benzyl-2,3-bis-(4,5-diamino-pyrazole-1-yl)-propionamide; 1,3-bis-(4,5-diamino-pyrazole-1-yl)-cyclohexane; 1,4-bis-(4,5-diamino-pyrazole-1-yl-methyl)-benzene; 1,4-bis-(4,5-diamino-pyrazole-1-yl-methyl)-2,5-dimethoxy-benzene; 1,3-bis-(4,5-diamino-pyrazole-1-yl-methyl)-benzene; 2,6-bis-(4,5-diamino-pyrazole-1-yl-methyl)-4-methyl-phenol; 1,2-bis-(4,5-diamino-pyrazole-1-yl-methyl)-benzene; 1,2-bis-(4,5-diamino-pyrazole-1-yl-methyl)-4,5-dimethoxy-benzene; 2,3-bis-(4,5-diamino-pyrazole-1-yl-methyl)-naphthalene; 2,3-bis-(4,5-diamino-pyrazole-1-yl-methyl)-anthracene; 9,10-bis-(4,5-diamino-pyrazole-1-yl-methyl)-anthracene; 4,4'-bis-(4,5-diamino-pyrazole-1-yl-methyl)-biphenyl; 1,2-bis-[4-(4,5-diamino-pyrazole-1-yl-methyl)-phenyl]-ethane; 2,5-bis-(4,5-diamino-pyrazole-1-yl-methyl)-furan; 2,5-bis-(4,5-diamino-pyrazole-1-yl-methyl)-thiophene; 2,8-bis-(4,5-diamino-pyrazole-1-yl-methyl)-dibenzothiophene; 4,4'-bis-(4,5-diamino-pyrazole-1-yl-methyl)-[2,2']bipyridyl and 1,2-bis-[6-(4,5-diamino-pyrazole-1-yl-methyl)-pyridine-2-yl]-ethane or their salts with organic and inorganic acids.

As preferred resorcinol derivatives of Formula (IV), 4-alkylresorcinols, such as 4-ethylresorcinol, 4-methylresorcinol, 2,4-dimethylresorcinol and 4-hexylresorcinol, in particular, may be mentioned.

The 4,5-diaminopyrazole of Formulas (I), (II) or (III), as well as the resorcinol derivative of Formula (IV) are contained in the inventive dyeing agent in each case in a total amount of 0.005 to 20% by weight, an amount of 0.01 to 10% by weight and, in particular, of 0.1 to 6% by weight being preferred.

Aside from the above-mentioned 4,5-diaminopyrazole derivatives, the inventive agent may also contain further developer substances. Particularly suitable for this purpose are 1,4-diamino-benzene (p-phenylenediamine), 1,4-diamino-2-methylbenzene (p-toluylenediamine), 1,4-diamino-2,6-dimethylbenzene, 1,4-diamino-2,5-dimethylbenzene, 1,4-diamino-2,3-dimethylbenzene, 2-chloro-1,4-diaminobenzene, 4-phenyl-amino-aniline, 4-dimethylamino-aniline, 4-diethylamino-aniline, 4-[di(2-hydroxyethyl)amino]-aniline, 4-[(2-methoxyethyl)amino]-aniline, 4-[(3-hydroxypropyl)amino]-aniline, 1,4-diamino-2-(2-hydroxyethyl)-benzene, 1,4-diamino-2-(1-hydroxyethyl)-benzene, 1,4-diamino-2-(1-methylethyl)-benzene, 1,3-bis[(4-aminophenyl)-(2-hydroxyethyl)amino]-2-propanol, 1,8-bis(2,5-diaminophenoxy)-3,6-dioxaoctane, 4-amino-phenol, 4-amino-3-methyl-phenol, 4-methylamino-phenol, 4-amino-2-(aminomethyl)-phenol, 4-amino-2-[(2-hydroxyethyl)-amino]methyl-phenol, 4-amino-2-(methoxy-methyl)-phenol, 4-amino-2-(2-hydroxyethyl)-phenol, 5-amino-salicylic acid, 2,5-diamino-pyridine, 2,4,5,6-tetraamino-pyrimidine, 2,5,6-triamino-4-(1H)-pyrimidone, 2-aminophenol, 2-amino-6-methyl-phenol and 2-amino-5-methyl-phenol or their salts.

Moreover, in addition to the above-mentioned resorcinol derivatives, the inventive dyeing agent may also contain further coupler substances, which are suitable for forming an oxidation dye. For this purpose, m-diamines, m-aminophenols, polyphenols or napthols, for example, may be used. Particularly suitable are N-(3-dimethylamino-phenyl)-urea, 2,6-diamino-pyridine, 2-amino-4-[(2-hydroxyethyl)-amino]-anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxy-ethyl)amino]-1,5-dimethoxybenzene, 2,3-diamino-6-methoxy-pyridine, 3-amino-6-methoxy-2-(methylamino)-pyridine, 2,6-diamino-3,5-dimethoxy-pyridine, 3,5-diamino-2,6-dimethoxy-pyridine, 1,3-diaminobenzene, 2,4-diamino-1-(2-hydroxyethoxy)-benzene, 2,4-diamino-1-(3-hydroxypropoxy)-benzene, 2,4-diamino-1-(3-methoxypropoxy)-benzene, 1-(2-aminoethoxy)-2,4-diaminobenzene, 2-amino-1-(2-hydroxyethoxy)-4-methylaminobenzene, 2,4-diaminophenoxy-acetic acid, 3-[di(2-hydroxy-ethyl)amino]-aniline, 4-amino-2-di[(2-hydroxyethyl)amino]-1-ethoxybenzene, 5-methyl-2-(1-methylethyl)-phenol, 3-[(2-hydroxyethyl)amino]-aniline, 3-[(2-aminoethyl)-amino]-aniline, 1,3-di(2,4-diaminophenoxy)-propane, di(2,4-diaminophenoxy)-methane, 1,3-diamino-2,4-dimethoxybenzene, 2,6-bis(2-hydroxyethyl)amino-toluene, 4-hydroxyindole, 3-dimethylamino-phenol, 3-diethylamino-phenol, 5-amino-2-methyl-phenol, 5-amino-4-fluoro-2-methyl-phenol, 5-amino-4-methoxy-2-methyl-phenol, 5-amino-4-ethoxy-2-methyl-phenol, 3-amino-2,4-dichloro-phenol, 5-amino-2,4-dichloro-phenol, 3-amino-2-methyl-phenol, 3-amino-2-chloro-6-methyl-phenol, 3-amino-phenol, 2-[(3-hydroxyphenyl)-amino]-acetamide, 5-[(2-hydroxy-ethyl)amino]-2-methyl-phenol, 3-[(2-hydroxyethyl)amino]-phenol, 3-[(2-methoxyethyl)amino]-phenol, 5-amino-2-ethyl-phenol, 2-(4-amino-2-hydroxyphenoxy)-ethanol, 5-[(3-hydroxypropyl)amino]-2-methyl-phenol, 3-[(2,3-dihydroxypropyl)-amino]-2-methyl-phenol, 3-[(2-hydroxyethyl)-amino]-2-methyl-phenol, 2-amino-3-hydroxy-pyridine, 5-amino-4-chloro-2-methyl-phenol, 1-naphthol, 1,5-dihydroxy-naphthalene, 1,7-dihydroxy-naphthalene, 2,3-dihydroxy-naphthalene, 2,7-dihydroxy-naphthalene, 2-methyl-1-naphthol-acetate, 3,4-methylenedioxy-phenol, 3,4-methylenedioxy-aniline, 5-[(2-hydroxyethyl)-amino]-1,3-benzodioxol, 6-bromo-1-hydroxy-3,4-methylenedioxybenzene, 3,4-diamino-benzoic acid, 3,4-dihydro-6-hydroxy-1,4(2H)-benzooxazine, 6-amino-3,4-dihydro-1,4(2H)-benzooxazine, 5,6-dihydroxy-indole, 5,6-dihydroxy-indoline, 4-hydroxy-indole, 5-hydroxy-indole, 6-hydroxy-indole, 7-hydroxy-indole and 2,3-indolindione, or their salts.

The above-mentioned additional developer and coupler substances are contained in the dyeing agent in each case in a total amount of 0.01 to 20% by weight, preferably of 0.1 to 10% by weight and particularly of 0.1 to 5% by weight.

Moreover, the dyeing agent may optionally contain additional, conventional, substantive anionic, cationic, zwitterionic or nonionic dyes. The preferred anionic dyes include, for example, disodium 6-hydroxy-5-[(4-sulfophenyl)azo]-2-naphthalenesulfonate (CI15985; Food Yellow No. 3; FD&C Yellow No. 6), disodium 2,4-dinitro-1-naphthol-7-sulfonate (CI10316; Acid Yellow No. 1; Food Yellow No. 1), 2-(indane-1,3-dione-2-yl)quinoline-x,x-sulfonic acid (mixture of mono-and disulfonic acid) (CI47005; D&C Yellow No. 10; Food Yellow No. 13, Acid Yellow No. 3), trisodium 5-hydroxy-1-(4-sulfophenyl)-4-[(4-sulfophenyl)azo]-pyrazole-3-carbonate (CI19140; Food Yellow No 4; Acid Yellow No. 23), 9-(2-carboxyphenyl)-6-hydroxy-3H-xanthene-3-one (CI45350; Acid Yellow No. 73; D&C Yellow No. 8), sodium 5-[(2,4-dinitro-phenyl)amino]-2-phenylamino-benzenesulfonate (CI10385; Acid Orange No. 3), monosodium 4-[(2,4-dihydroxyphenyl)azo]-benzenesulfonate (CI14270; Acid Orange No. 6), sodium 4-[(2-hydroxynaphth-1-yl)azo]-benzenesulfonate (CI15510; Acid Orange No. 7), sodium 4-[(2,4-dihydroxy-3-[(2,4-dimethylphenyl)azo]phenyl)azo]-benzenesulfonate (CI20170; Acid Orange No. 24), disodium 4-hydroxy-3-[(4-sulfonaphth-1-yl)azo]-1-naphthalene-sulfonate (CI14720; Acid Red No. 14), trisodium 6-hydroxy-5-[(4-sulfonaphth-1-yl)azo]-2,4-naphthalene-disulfonate (CI16255; Ponceau 4R; Acid Red No. 18), trisodium 3-hydroxy-4-[(4-sulfonaphth-1-yl)azo]-2,7-naphthalene-disulfonate (CI16185; Acid Red No. 27), disodium 8-amino-1-hydroxy-2-(phenylazo)-3,6-naphthalene-disulfonate (CI17200; Acid Red No. 33), disodium 5-(acetylamino)-4-hydroxy-3-[(2-methylphenyl)-azo]-2,7-naphthalene-disulfonate (CI18065; Acid Red No. 35), disodium 2-(3-hydroxy-2,4,5,7-tetraiod-dibenzopyran-6-one-9-yl)-benzoic acid (CI45430; Acid Red No. 51), N-[6-(diethylamino)-9-(2,4-disulfophenyl)-3H-xanthene-3-ylidene]-N-ethylethane aminium hydroxide, internal sodium salt (CI45100; Acid Red No. 52), disodium 8-[(4-(phenylazo)-phenyl)azo]-7-naphthol-1,3-disulfonate (CI27290; Acid Red No. 73), disodium 2',4',5',7'-tetrabromo-3', 6'-dihydroxyspiro[isobenzofuran-1(3H),9'-[9H]xanthene]-3-one (CI45380; Acid Red No. 87), disodium 2',4',5',7'-tetrabromo-4,5,6,7-tetrachloro-3',6'-dihydroxyspiro[isobenzofuran-1(3H),9'[9H]xanthene]-3-one (CI45410; Acid Red N. 92), disodium 3', 6'-dihydroxy-4',5'-diiodospiro-[isobenzofuran-1(3H),9'(9H)-xanthene)-3-one (CI45425; Acid Red No. 95), disodium (2-sulfophenyl)di[4-(ethyl((4-sulfophenyl)methyl)amino)-phenyl]-carbenium, betaine (CI42090; Acid Blue No. 9; FD&C Blue No. 1), disodium 1,4-bis[(2-sulfo-4-methylphenyl)amino]-9,10-anthraquinone (CI61570; Acid Green No. 25), internal monosodium salt of bis[4-(dimethylamino)-phenyl]-(3,7-disulfo-2-hydroxy-naphth-1-yl)carbenium, (CI44090; Food Green No. 4; Acid Green No. 50), internal sodium salt of bis[4-(diethylamino) phenyl]( 2,4-disulfophenyl)-carbenium (2:1) (CI42045; Food Blue No. 3; Acid Blue No. 1), internal calcium salt of bis[4-(diethylamino)phenyl](5-hydroxy-2,4-disulfophenyl)-carbenium (2:1) (CI4205 1; Acid Blue No. 3), sodium 1-amino-4-(cyclohexylamino)-9,10-anthraquinone-2-sulfonate (CI62045; Acid Blue No. 62), disodium 2-(1,3-dihydro-3-oxo-5-sulfo-2H-indole-2-ylidene)-2,3-dihydro-3-oxo-1H-indole-5-sulfonate (CI73015; Acid Blue No. 74), internal monosodium salt of 9-(2-carboxyphenyl)-3-[(2-methylphenyl)-amino]-6-[(2-methyl-4-sulfophenyl)amino] xanthylium (CI45190; Acid Violet No. 9), sodium 1-hydroxy-4-[(4-methyl-2-sulfophenyl)amino]-9,10-anthraquinone (CI60730; D&C Violet No. 2; Acid Violet No. 43), bis[3-nitro-4-[(4-phenylamino)-3-sulfo-phenylamino]-phenyl]-sulfone (CI10410; Acid Brown No. 13), disodium 5-amino-4-hydroxy-6-[(4-nitrophenyl)azo]-3-(phenylazo)-2,7-naphthalenedisulfonate (CI20470; Acid Black No. 1), chromium complex of 3-hydroxy-4-[(2-hydroxynaphth-1-yl)azo]-7-nitro-1-naphthalenesulfonate (3:2) (CI15711; Acid Black No. 52), disodium 3-[(2,4-dimethyl-5-sulfophenyl)azo]-4-hydroxy-1-naphthalenesulfonate (CI14700; Food Red No. 1; Ponceau SX; FD&C Red No. 4), tetrasodium 4-(acetylamino)-5-hydroxy-6-[(7-sulfo-4-[(4-sulfophenyl)azo]naphth-1-yl)azo]-1,7-naphthalenedisulfonate (CI28440; Food Black No. 1) and chromium complex of sodium 3-hydroxy-4-(3-methyl-5-oxo-1-phenyl-4,5-dihydro-1H-pyrazole-4-ylazo)-naphthalene-1 sulfonate (Acid Red No. 195).

The preferred cationic dyes include, for example, 9-(dimethylamino)-benzo[a]phenoxazine-7-ium chloride (CI51175; Basic Blue No. 6), di[4-(diethylamino)phenyl][4-(ethylamino)naphthyl]carbenium chloride (CI42595; Basic Blue No. 7), 3,7-di(dimethylamino)phenothiazine-5-ium chloride (CI52015; Basic Blue No. 9), di[4-(dimethylamino) phenyl][4-(phenylamino)-naphthyl]carbenium chloride (CI44045; Basic Blue No. 26), 2-[(4-(ethyl(2-hydroxyethyl)amino)phenyl)-azo]-6-methoxy-3-methyl-benzothiazolium methyl sulfate (CI11154; Basic Blue No. 41), 8-amino-2-bromo-5-hydroxy-4-imino-6-[(3-(trimethylammonio)phenyl)amino]-1(4H)-naphthalinone chloride (CI56059; Basic Blue No.99), bis[4-(dimethylamino)-phenyl][ 4-(methylamino)phenyl]-carbenium chloride (CI42535; Basic Violet No. 1), tris(4-amino-3-methylphenyl)-carbenium chloride (CI42520; Basic Violet No. 2), tris[4-(dimethylamino)-phenyl]carbenium chloride (CI42555; Basic Violet No. 3), 2-[3,6-(diethylamino)dibenzopyranium-9-yl]-benzoic acid chloride (CI45170; Basic Violet No. 10), di(4-aminophenyl) (4-amino-3-methylphenyl)carbenium chloride (CI42510; Basic Violet No. 14), 1,3-bis[(2,4-diamino-5-methylphenyl) azo]-3-methylbenzene (CI21010; Basic Brown No. 4), 1-[(4-aminophenyl)azo]-7-(trimethylammonio)-2-naphthol chloride (CI12250; Basic Brown No. 16),1-[(4-amino-2-nitrophenyl)azo]-7-(trimethylammonio)-2-naphthol chloride (CI12251; Basic Brown No. 17), 1-[(4-amino-3-nitrophenyl)azo]-7-(trimethylammonio)-2-naphthol chloride (CI12251; Basic Brown No. 17), 3,7-diamino-2,8-dimethyl-5-phenyl-phenazinium chloride (CI50240; Basic Red No. 2), 1,4-dimethyl-5-[(4-(dimethylamino)phenyl)azo]-1,2,4-triazolium chloride (CI11055; Basic Red No. 22), 2-hydroxy-1-[(2-methoxy-phenyl)azo]-7-(trimethylammonio)-naphthalene chloride (CI12245; Basic Red No. 76), 2-[2-((2,4-dimethoxy-phenyl)amino)ethenyl]-1,3,3-trimethyl-3H-indole-1-ium chloride (CI48055; Basic Yellow No. 11), 3-methyl-1-phenyl-4-[(3-(trimethylammonio)phenyl)-azo]-pyrazole-5-one chloride (CI12719; Basic Yellow No. 57) and bis[4-(diethylamino)phenyl]phenylcarbenium hydrogen sulfate (1:1) (CI42040; Basic Green No. 1).

As suitable nonionic dyes, especially for improved color equalization and for producing special nuances, the following, for example, may be mentioned: 1-amino-2-[(2-hydroxyethyl)amino]-5-nitrobenzene (HC Yellow No. 5), 1-(2-hydroxyethoxy)-2-[(2-hydroxyethyl)-amino]-5-nitrobenzene (HC Yellow No. 4), 1-[(2-hydroxyethyl) amino]-2-nitrobenzene (HC Yellow No. 2), 2-[(2-hydroxyethyl)amino]-1-methoxy-5-nitrobenzene, 2-amino-3-nitro-phenol, 1-(2-hydroxyethoxy)-3-methylamino-4- nitrobenzene, 2,3-(dihydroxy-propoxy)-3-methylamino-4-nitrobenzene, 2-[(2-hydroxyethyl)amino]-5-nitrophenol (HC Yellow No. 11), 3-[(2-amino-ethyl)amino]-1-methoxy-4-nitrobenzene-hydrochloride (HC Yellow No. 9), 1-[(2-ureidoethyl)amino]-4-nitrobenzene, 4-[(2,3-dihydroxypropyl)amino]- 3-nitro-1-trifluoromethylbenzene (HC Yellow No. 6), 1-chloro-2,4-bis-[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)-amino]-3-nitrobenzonitrile (HC Yellow No. 14), 4-[(2-hydroxyethyl)amino]-3-nitro-benzamide (HC Yellow No. 15), 1-amino-4-[(2-hydroxyethyl)amino]-2-nitrobenzene (HC Red No. 7), 2-amino-4,6-dinitro-phenol, 2-ethylamino-4,6-dinitrophenol, 4-amino-2-nitro-diphenylamine (HC Red No. 1), 1-amino-4-[di(2-hydroxyethyl)amino]-2-nitrobenzene-hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-amino-3-nitrophenol, 4-[(2-hydroxyethyl)-amino]-3-nitrophenol, 1-[(2-aminoethyl)amino]-4-(2-hydroxyethoxy)-2-nitrobenzene (HC Orange No. 2), 4-(2,3-dihydroxy-propoxy)-1-[(2-hydroxy-ethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)amino]-4,6-dinitro-phenol, 4-ethylamino-3-nitrobenzoic acid, 2-[(4-amino-2-nitrophenyl)amino]-benzoic acid, 2-chloro-6-methylamino-4-nitrophenol, 2-chloro-6-[(2-hydroxyethyl)amino]-4-nitrophenol, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 1,2,3,4-tetrahydro-6-nitroquinoxaline, 7-amino-3,4-dihydro-6-nitro-2H-1,4-benzooxazine (HC Red No. 14), 1,4-bis[(2-hydroxyethyl)amino]-2-nitrobenzene, 1-(2-hydroxyethyl)amino-2-nitro-4-[di(2-hydroxyethyl)amino]-benzene (HC Blue No. 2), 1-amino-3-methyl-4-[(2-hydroxyethyl)amino]-6-nitrobenzene (HC Violet No. 1), 4-[ethyl-(2-hydroxyethyl)amino]-1-[(2-hydroxyethyl)amino]-2-nitrobenzene-hydrochloride (HC Blue No. 12), 4-[di(2-hydroxyethyl)amino]-1-[(2-methoxyethyl)amino]-2-nitrobenzene (HC Blue No. 11), 1-[(2,3-dihydroxy-propyl)amino]-4-[methyl-(2-hydroxyethyl)-amino]-2-nitrobenzene (HC Blue No. 10), 1-[(2,3-dihydroxypropyl)amino]-4-[ethyl-(2-hydroxyethyl)amino]-2-nitrobenzene-hydrochloride (HC Blue No. 9), 1-(3-hydroxypropylamino)-4-[di(2-hydroxyethyl)amino]-2-nitrobenzene (HC Violet No. 2), 1-methylamino-4-[methyl-(2,3-dihydroxypropyl)amino]-2-nitrobenzene (HC Blue No. 6), 2-((4-amino-2-nitrophenyl)amino)-5-dimethyl-amino-benzoic acid (HC Blue No. 13), 1,4-di[(2,3-dihydroxypropyl)amino]-9,10-anthraquinone, 1-[(2-hydroxyethyl)amino]-4-methylamino-9,10-anthraquinone (CI61505, Disperse Blue No. 3), 2-[(2-aminoethyl)amino]-9,10-anthraquinone (HC Orange No. 5), 1-hydroxy-4-[(4-methyl-2-sulfo-phenyl)amino]-9,10-anthraquinone, 1-[(3-aminopropyl)amino]-4-methyl-amino-9,10-anthraquinone (HC Blue No. 8), 1-[(3-aminopropyl)amino]-9,10-anthraquinone (HC Red No. 8), 1,4-diamino-2-methoxy-9,10-anthraquinone (CI62015, Disperse Red No. 11, Solvent Violet No. 26), 1,4-dihydroxy-5,8-bis[(2-hydroxyethyl)amino]-9,10-anthraquinone (CI62500, Disperse Blue No. 7, Solvent Blue No. 69), 1-[di(2-hydroxyethyl)amino]-3-methyl-4-[(4-nitrophenyl)azo]-benzene (CI1210, Disperse Red No. 17), 4-[(4-amino-phenyl)azo]-1-[di(2-hydroxyethyl)amino]-3-methylbenzene (HC Yellow No. 7), 2,6-diamino-3-[(pyridine-3-yl)azo]-pyridine, 2-((4-(acetylamino)phenyl)-azo)-4-methylphenol (CI11855; Disperse Yellow No. 3).

From the group of substantive dyes, special mention is given to 2-amino-4,6-dinitrophenol, 2-ethylamino-4,6-dinitrophenol and 2-[(2-hydroxy-ethyl)amino)-4,6-dinitrophenol, as well as to dyes of the general Formula (V),

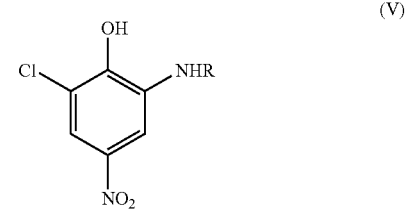

in which R represents hydrogen, ethyl, methyl or hydroxyethyl.

The substantive dyes may be used in the dyeing agent in an amount of about 0.01 to 10% by weight and preferably of 0.1 to 5% by weight.

Of course, the dyes, insofar as they are bases, may also be used in the form of their physiologically tolerated salts with organic or inorganic acids, such as hydrochloric or sulfuric acid or, insofar as they have aromatic OH groups, in the form of the salts with bases, such as alkali phenolates.

The above-described, inventive combinations of compounds of Formulas (I) to (III) and (IV), as well as, optionally, further oxidative hair-dyeing precursors and/or substantive dyes, are applied in a suitable dye carrier composition for the dyeing.

Moreover, the dyeing agent may contain further conventional additives, for example, antioxidants such as ascorbic acid, thioglycolic acid or sodium sulfite, as well as perfume oils, penetrants, buffer systems, complexing agents, preservatives, wetting agents, emulsifiers and care materials.

The inventive dyeing agent may be prepared, for example, in the form of a solution, especially an aqueous or an aqueous alcoholic solution. However, the particularly preferred forms of preparation are creams, gels or emulsions. Their composition represents a mixture of the dye components with conventional additives for such preparations.

Conventional additives in solutions, creams, emulsions or gels are, for example, solvents such as water, low molecular weight aliphatic alcohols, such as ethanol, n-propanol or isopropanol, glycerin or glycols such as 1,2-dihydroxypropane, furthermore wetting agents or emulsifiers from the classes of anionic, cationic, amphoteric or nonionic surface active substances, such as fatty alcohol sulfates, ethoxylated fatty alcohol sulfates, alkyl sulfonates, alkylbenzenesulfonates, alkyltrimethylammonium salts, alkyl betaines, ethoxylated fatty alcohols, ethoxylated nonylphenols, fatty acid alkanolamides and ethoxylated esters of fatty acids, furthermore thickeners such as higher molecular weight fatty alcohols, starch, cellulose derivatives, petrolatum, paraffin oil and fatty acids, as well as care materials, such as cationic resins, lanolin derivatives, cholesterol, pantothenic acid and betaine. The components mentioned are used in amounts, customary for such purposes; for example, the wetting agents and emulsifiers are used in concentrations of 0.1 to 30% by weight, the thickeners are used in an amount of about 0.1 to 30% by weight and the care materials are used in a concentration of about 0.1 to 5.0% by weight.

The ready-for-use inventive hair-dyeing agent is produced by mixing the dye carrier combination with an oxidizing agent immediately before these materials are applied.

As oxidizing agent, primarily hydrogen peroxide or its addition compounds with urea, melamine, sodium borate or sodium carbonate in the form of a 1 to 12% and preferably of 3 to 6% aqueous solution, comes into consideration. The ratio by weight of hair dyeing agent to oxidizing agent preferably is 5:1 to 1:3 and especially 1:1 to 1:2 here. Larger amounts of oxidizing agents are used especially for higher dye concentrations in the hair dyeing agent or if, at the same time, the hair is to be bleached more. In principle, it is also possible to use oxygen from the air instead of the aforementioned oxidizing agent to oxide the dye.

When the dye carrier composition (the pH of which is about 6 to 11.5) is mixed with the generally acidic oxidizing agent (the pH of which is about 2 to 6.5), the pH of the ready-for-use inventive hair dyeing agent adjusts to a value, which is determined by the amounts of alkali in the dye carrier composition and the amounts of acid in the oxidizing agent, as well as by the mixing ratio. Depending on the composition, the inventive dyeing agent may be weakly acidic, neutral or alkaline and, in the ready-for-use state, have a pH of about 3 to 11 and preferably of about 5 to 10. The pH is adjusted to a basic value here preferably with ammonia. However, organic amines, such as 2-amino-2-methyl-1-propanol, tris(hydroxymethyl)amino-methane, monoethanolamine and triethanolamine, or also inorganic bases such as sodium hydroxide and potassium hydroxide may also be used. For adjusting the pH to an acidic range, inorganic or organic acids, such as phosphoric acid, acetic acid, lactic acid, ascorbic acid, citric acid or tartaric acid come into consideration.

Subsequently, an amount of this mixture, which is sufficient for the dyeing treatment of the hair and, depending upon the fullness of the hair, ranges from about 60 to 200 gram, is applied on the hair and allowed to act for about 10 to 45 minutes and preferably for 30 minutes at a temperature preferably of 30° to 40° C. on the hair, after with the hair is rinsed with water and dried. Optionally, at the conclusion of this rinsing, the hair is washed with a shampoo and possibly rinsed with a weak organic acid, such as citric acid or tartaric acid. Subsequently, the hair is dried.

The dyeing agent, containing the inventive combination of 4,5-diaminopyrazoles of Formulas (I), (II) or (III) and resorcinol derivatives of Formula (IV) enables the hair to be dyed from orange to red with outstanding color fasteners, especially with regard to the "bleeding behavior", as well as the wash, light and crocking fasteners. The color shades are distinguished here especially by their color intensity and luminosity.

The following Examples are intended to explain the object in greater detail, without limiting it to these Examples.

EXAMPLES

Examples 1.1 to 1.15

Hair Dyeing Preparation

| | |
|---|---:|
| 4,5-Diaminopyrazole derivative of Formula (I) to (III) | Quantitative data in TABLE 1 |
| Resorcinol derivative of Formula (IV) | Quantitative data in TABLE 1 |
| Sodium hydroxide (10% aqueous solution) | 0.74 g |
| Sodium sulfite | 0.40 g |
| Ascorbic acid | 0.30 g |
| Disodium ethylenediaminetetraacetate | 0.30 g |
| Lauryl ether sulfate, (28% aqueous solution) | 10.0 g |
| Ethanol | 8.00 g |
| Ammonia (25% aqueous solution) | 9.20 g |
| Water, fully desalinated | ad 100.00 g |

The above dye carrier composition (5 g) is mixed with 5 g of a 6% hydrogen peroxide solution. The ready-for-use oxidation hair-dyeing agent obtained is applied on the strands of hair and distributed uniformly with a brush. After a period of action of 20 minutes at 40° C., the hair is rinsed with lukewarm water and then dried.

The hair, dyed with the above dyeing agents, exhibits very good "bleeding behavior" and does not stain even in the moist state. The dyeing results are summarized in the following Table 1.

Examples 2.1 to 2.3

Checking the "Bleeding Behavior"

| | |
|---|---:|
| 4,5-Diaminopyrazole derivative of Formulas (I) or (II) | Quantitative data in TABLE 2 |
| Resorcinol derivative of Formula (IV) | Quantitative data in TABLE 2 |
| Sodium hydroxide (10% aqueous solution) | 0.74 g |
| Sodium sulfite | 0.40 g |
| Ascorbic acid | 0.30 g |
| Disodium ethylenediaminetetraacetate | 0.30 g |
| Lauryl ether sulfate, (28% aqueous solution) | 10.0 g |
| Ethanol | 8.00 g |
| Ammonia (25% aqueous solution) | 9.20 g |
| Water, fully desalinated | ad 100.00 g |

The above dye carrier composition (5 g) is mixed with 5 g of a 6% hydrogen peroxide solution. The ready-for-use oxidation hair-dyeing agent obtained is applied on the strands of hair and distributed uniformly with a brush. After a period of action of 20 minutes at 40° C., the hair is rinsed with lukewarm water and then dried.

For the washing test, the dyed strands are each stirred for 5 hours in 300 mL of fully deionized water.

The dyeing and washing results are summarized in the following Table 2.

Examples 3.1 to 3.6

Hair Dyeing Agent

| | |
|---|---:|
| 4,5-Diaminopyrazole derivative of Formulas (I) to (III) | Quantitative data in TABLE 3 |
| Additional developer substances | Quantitative date in TABLE 3 |
| Resorcinol derivative of Formula (IV) | Quantitative data in TABLE 3 |
| Additional coupler substances | Quantitative data in TABLE 3 |
| Sodium hydroxide (10% aqueous solution) | 2.00 g |
| Sodium sulfite | 0.40 g |
| Ascorbic acid | 0.30 g |
| Disodium ethylenediaminetetraacetate | 0.30 g |
| Lauryl ether sulfate, (28% aqueous solution) | 10.0 g |
| Ethanol | 8.00 g |
| Ammonia (25% aqueous solution) | 9.20 g |
| Water, fully desalinated | ad 100.00 g |

The above dye carrier composition (5 g) is mixed with 5 g of a 6% hydrogen peroxide solution. The ready-for-use oxidation hair-dyeing agent obtained is applied on the strands of hair and distributed uniformly with a brush. After a period of action of 20 minutes at 40° C., the hair is rinsed with lukewarm water and then dried.

The hair, dyed with the above dyeing agents, exhibits very good "bleeding behavior" and does not stain even in the moist state. The dyeing results are summarized in the following Table 3.

The L*a*b* color values, given in the present examples, were determined with a Minolta, Type II Chromameter.

The "L" value represents the brightness (that is, the lower the "L" value, the greater is the intensity of the color), whereas the "a" value is a measure of the red portion (the red portion varies with the value of "a"). The "b" value is a measure of the blue portion of the color (the more negative the value of "b", the greater is the blue portion).

Unless stated otherwise, all percentages in the present application are percentages by weight.

TABLE 1

| No. | Developer/Coupler Combination | Shade after the Dyeing | Measured Color Values of Strand of Hair | L | a | b |
|---|---|---|---|---|---|---|
| 1.1 | 4,5-diamino-1-((4-methoxy-phenyl)methyl)-1H-pyrazole-dihydrochloride: 2.80 g; 4-ethylresorcinol: 1.38 g | red | Before dyeing: After dyeing: | +83.30; +30.58; | −0.48; +46.03; | +10.40 +20.38 |
| 1.2 | 4,5-diamino-1-((4-methoxy-phenyl)methyl)-1H-pyrazole-dihydrochloride: 2.80 g; 2,4-dimethylresorcinol: 1.38 g | red orange | Before dyeing: After dyeing: | +83.30; +37.14; | −0.48; +53.74; | +10.40 +29.76 |
| 1.3 | 4,5-diamino-1-benzyl-1H-pyrazole-sulfate (2:1): 2.28 g; 4-ethylresorcinol: 1.38 g | rust red | Before dyeing: After dyeing: | +83.30; +33.01; | −0.48; +46.63; | +10.40 +23.05 |
| 1.4 | 4,5-diamino-1-pentyl-1H-pyrazole-dihydrochloride: 2.32 g; 4-ethylresorcinol: 1.38 g | red orange | Before dyeing: After dyeing: | +83.30; +32.68; | −0.48; +51.06; | +10.40 +23.86 |
| 1.5 | 4,5-diamino-1-(2-hydroxyethyl)-1H-pyrazole-sulfate (1:1): 2.30 g; 4-ethylresorcinol: 1.38 g | pink orange | Before dyeing: After dyeing: | +83.30; +39.29; | −0.48; +56.09; | +10.40 +32.37 |
| 1.6 | 4,5-diamino-1-(2-hydroxyethyl)-1H-pyrazole-sulfate (1:1): 2.30 g; 2,4-dimethylresorcinol: 1.38 g | red orange | Before dyeing: After dyeing: | +83.30; +39.76; | −0.48; +55.71; | +10.40 +32.32 |
| 1.7 | 4,5-diamino-1-(4-methylbenzyl)-1H-pyrazole-hemisulfate: 2.41 g; 4-ethylresorcinol: 1.38 g | red orange | Before dyeing: After dyeing: | +83.30; +33.70; | −0.48; +47.78; | +10.40 +24.27 |
| 1.8 | 1,2-bis-(4,5-diamino-1H-pyrazole-1-yl)-ethane: 3.53 g; 4-ethylresorcinol: 1.38 g | red orange | Before dyeing: After dyeing: | +83.30; +34.45; | −0.48; +41.34; | +10.40 +23.99 |
| 1.9 | 1,2-bis-(4,5-diamino-1H-pyrazole-1-yl)ethane: 3.53 g; 2,4-dimethylresorcinol: 1.38 g | red orange | Before dyeing: After dyeing: | +83.30; +37.89; | −0.48; +46.09; | +10.40 +27.96 |
| 1.10 | 1,4-bis-(4,5-diamino-pyrazole-1-yl-methyl)-benzene tetrachloride: 4.27 g; 4-ethylresorcinol: 1.38 g | red orange | Before dyeing: After dyeing: | +83.30; +39.42; | −0.48; +48.56; | +10.40 +29.19 |
| 1.11 | 1,4-bis-(4,5-diamino-pyrazole-1-yl-methyl)-benzene tetrachloride: 4.27 g; 2,4-dimethylresorcinol: 1.38 g | red orange | Before dyeing: After dyeing: | +83.30; +42.15; | −0.48; +50.82; | +10.40 +30.06 |
| 1.12 | 4,5-diamino-1-(2-hydroxyethyl)-1H-pyrazole-sulfate (1:1): 2.30 g; 4-methylresorcinol: 1.38 g | red orange | Before dyeing: After dyeing: | +83.30; +39.28; | −0.48; +47.80; | +10.40 +28.48 |
| 1.13 | 4,5-diamino-1-(4-methylbenzyl)-1H-pyrazole-hemisulfate: 2.41 g; 4-methylresorcinol: 1.24 g | red orange | Before dyeing: After dyeing: | +83.30; +33.62; | −0.48; +46.89; | +10.40 +24.14 |
| 1.14 | 4,5-diamino-1-(2-hydroxyethyl)-1H-pyrazole-sulfate (1:1): 2.30 g; 4-hexylresorcinol: 1.94 g | red orange | Before dyeing: After dyeing: | +83.30; +39.28; | −0.48; +47.80; | +10.40 +28.48 |
| 1.15 | 4,5-diamino-1-(4-methylbenzyl)-1H-pyrazole-hemisulfate: 2.41 g; 4-hexylresorcinol: 1.94 g | red orange | Untreated hair: After the coloring: | +83.30; +31.43; | −0.48; +38.57; | +10.40 +16.80 |

TABLE 2

| No. | Developer/Coupler Combination | Shade after the Dyeing | Measured Color Values of Strand of Hair | L | a | b |
|---|---|---|---|---|---|---|
| 2.1 | 4,5-diamino-1-benzyl-1H-pyrazole-sulfate (2:1): 2.28 g; 2,4-dimethylresorcinol: 1.38 g | red orange | Before dyeing: | +83.30; | −0.48; | +10.40 |
|  |  |  | After dyeing: | +36.33; | +53.49; | +29.45 |
|  |  |  | After 5 hours washing with demineralized water: | +36.60; | +50.77; | +28.12 |
| 2.2 | 4,5-diamino-1-pentyl-1H-pyrazole-dihydrochloride: 2.32 g; 2,4-dimethylresorcinol: 1.38 g | red orange | Before dyeing: | +83.30; | −0.48; | +10.40 |
|  |  |  | After dyeing: | +34.64; | +55.85; | +26.83 |
|  |  |  | After 5 hours washing with demineralized water: | +36.23; | +53.15; | +27.15 |
| 2.3 | 4,5-diamino-1-(4-methylbenzyl)-1H-pyrazole-hemisulfate: 2.41 g; 2,4-dimethylresorcinol: 1.38 g | red orange | Before dyeing: | +83.30; | −0.48; | +10.40 |
|  |  |  | After dyeing: | +35.48; | +53.43; | +27.73 |
|  |  |  | After 5 hours washing with demineralized water: | +34.76; | +50.34; | +26.69 |

TABLE 3

| No. | Developer/Coupler Combination | Shade after the Dyeing | Measured Color Values of Strand of Hair | L | a | b |
|---|---|---|---|---|---|---|
| 3.1 | 4,5-diamino-1-(2-hydroxyethyl)-1H-pyrazole-sulfate (1:1): 1.20 g; 1,4-diamino-2-methylbenzene-sulfate (1:1): 1.10 g 4-ethylresorcinol: 1.38 g 5-amino-2-methyl-phenol: 0.62 g | rust brown | Before dyeing: After dyeing: | +83.30; +20.44; | −0.48; +19.71; | +10.40 +4.41 |
| 3.2 | 4,5-diamino-1-(2-hydroxyethyl)-1H-pyrazole-sulfate (1:1): 1.20 g; 2,5-diamino-benzene ethanol-sulfate: 1.25 g 2,4-dimethylresorcinol: 1.38 g | orange brown | Before dyeing: After dyeing: | +83.30; +36.63; | −0.48; +38.53; | +10.40 +25.66 |
| 3.3 | 4,5-diamino-1-((4-methyl-phenyl)methyl)-1H-pyrazole-sulfate (2:1): 1.26 g; N,N-bis(2-hydroxyethyl)-p-phenylenediamine-monosulfate: 1.48 g; 4-methylresorcinol: 0.62 g 5-((2-hydroxyethyl)amino)-2-methoxy-aniline-sulfate (1:1): 1.40 g | dark brown | Before dyeing: After dyeing: | +83.30; +17.64; | −0.48; +0.70; | +10.40 −1.24 |
| 3.4 | 1,2-bis-(4,5-diamino-1H-pyrazole-yl)-ethane*4HCl: 1.84 g; 4-amino-3-methyl-phenol: 0.62 g 4-hexylresorcinol: 0.97 g 1-naphthalenol: 0.72 g | claret | Before dyeing: After dyeing: | +83.30; +20.53; | −0.48; +20.09; | +10.40 +2.32 |
| 3.5 | 4,5-diamino-1-(2-hydroxyethyl)-1H-pyrazole-sulfate (1:1): 1.20 g; 2,4-dimethylresorcinol: 0.28 g 1,3-dihydroxy-2-methylbenzene: 0.25 g 1,3-dihydroxybenzene: 0.22 g 3-amino-phenol: 0.22 g N,N-dimethyl-3-ureido-aniline: 0.36 g | brown red | Before dyeing: After dyeing: | +83.30; +23.39; | −0.48; +30.55; | +10.40 −8.42 |
| 3.6 | 1,4-bis-(4,5-diamino-1H-pyrazole-yl-methyl)-benzene *4HCl: 2.22 g; 1,4-diamino-2-methylbenzene-sulfate (1:1): 1.10 g 4-ethylresorcinol: 0.46 g N-(hydroxyethyl)-3,4-methylenedioxy-aniline-hydrochloride: 0.72 g | dark brown | Before dyeing: After dyeing: | +83.30; +17.50; | −0.48; +0.20; | +10.40 −0.27 |

TABLE 3-continued

| | Shade | | | |
| Developer/Coupler | after | Measured Color Values of Strand of Hair | | |
| No. Combination | the Dyeing | L | a | b |
|---|---|---|---|---|
| 1,3-diamino-4-(2-hydroxyethoxy)-benzene-sulfate (1:1): 0.80 g | | | | |

What is claimed is:

1. An agent for oxidative dyeing of keratin fibers, said agent comprising a combination of
    at least one 4,5-diaminopyrazole derivative of formula (I), (II) or (III), or a salt thereof with an organic or inorganic acid:

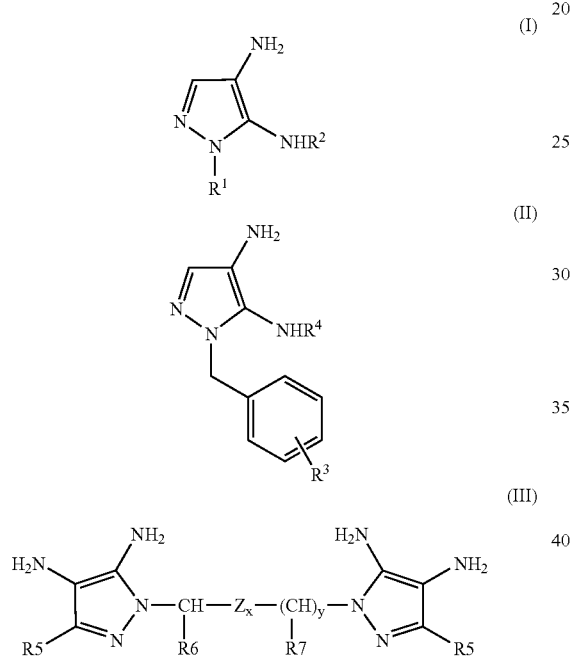

wherein $R^1$ and $R^2$ each, independently of each other; represent hydrogen, a linear or branched $C_1$–$C_6$ alkyl group, an optionally substituted phenyl group or a linear or branched $C_2$–$C_4$-hydroxyalkyl group; with the proviso that $R^1$ is not methyl if $R^2$ is hydrogen;

R3 represents a halogen atom, a linear or branched $C_1$–$C_4$ alkyl group or a linear or branched $C_1$–$C_4$ alkoxy group and $R^4$ represents hydrogen, a linear or branched $C_1$–$C_4$ alkyl group or a linear or branched $C_2$–$C_4$ hydroxyalkyl group;

$R^5$ represents hydrogen, a linear or branched $C_1$–$C_6$ alkyl group, a $C_1$–$C_4$ hydroxyalkyl group, a $C_1$–$C_4$ aminoalkyl group, a $C_1$–$C_8$ alkylamino group, a di($C_1$–$C_8$)alkylamino group, a $C_1$–$C_4$ alkylamino-($C_1$–$C_4$)alkyl group or a di($C_1$–$C_4$) alkylamino-($C_1$–$C_4$)alkyl group, an aryl group or a heteroaryl group;

$R^6$ and $R^7$ may be the same or different and independently of each other, each represent hydrogen, a linear or branched $C_1$–$C_6$ alkyl group, an aryl group, a heteroaryl group, a carboxylic acid group, a carboxylic ester group, an optionally substituted carboxylic acid amide group, a hydroxy group or a $C_1$–$C_4$ hydroxyalkyl group or $R^2$ and $R^3$ jointly form an optionally substituted $C_1$–$C_6$ alkylene group;

Z is a $C_1$–$C_{10}$ alkyl diradical, which is optionally interrupted by a hetero atom, an aromatic diradical or a heteroaromatic diradical, which is optionally condensed with one or two benzene rings and/or substituted by a hydroxy group or a $C_1$–$C_6$ alkyl group, or a diradical of formula —Ar(Alk)$_n$—Ar—, in which Ar is an optionally substituted aryl or heteroaryl group, Alk is a —CH$_2$ group and n is a whole number from 0 to 6; and x and y, independently of one another are equal to 0 or 1; and at least one resorcinol derivative, of formula (IV), which is substituted in at a 4 position thereof;

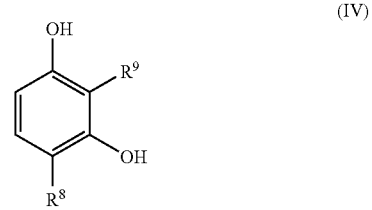

wherein $R^8$ is a linear or branched $C_1$–$C_8$ alkyl group, a linear or branched $C_1$–$C_8$ hydroxyalkyl group, a linear or branched $C_1$–$C_4$ alkoxy-($C_1$–$C_8$)alkyl group or a linear or branched $C_1$–$C_8$ aminoalkyl group; and $R^9$ represent hydrogen, a linear or branched $C_1$–$C_8$ alkyl group, a linear or branched $C_1$–$C_8$ hydroxyalkyl group, a linear or branched $C_1$–$C_4$ alkoxy-$C_1$–$C_8$ alkyl group or a linear or branched $C_1$–$C_8$ aminoalkyl group.

2. The agent as defined in claim 1, wherein said at least one 4,5-diaminopyrazole derivative is selected from the group consisting of 4,5-diamino-1-(4'-methylbenzyl)-pyrazole; 4,5-diamino-1-(3'-methylbenzyl)-pyrazole; 4,5-diamino-1-(2'-methylbenzyl)-pyrazole; 4,5-diamino-1-(2'-hydroxyethyl)-1H-pyrazole; 4,5-diamino-1-benzyl-1H-pyrazole; 4,5-diamino-1-ethyl-1H-pyrazole; 4,5-diamino-1-isopropyl-1H-pyrazole; 4,5-diamino-1-pentyl-1H-pyrazole; 4,5-diamino-1-(4'-methoxybenzyl)-1H-pyrazole; 4,5-diamino-1H-pyrazole; 4,5-diamino-1-(3'-methoxybenzyl)-1H-pyrazole; 4,5-diamino-1-(2'-methoxybenzyl)-1H-pyrazole; 4,5-diamino-1-(4'-chlorobenzyl)-1H-pyrazole; 4,5-diamino-1-(3'-chlorobenzyl)-1H-pyrazole; 4,5-diamino-1-(2'-chlorobenzyl)-1H-pyrazole; 4-amino-5-methylamino-1-(4'-methoxybenzyl)-1H-pyrazole; 4-amino-5-(2'-hydroxyethyl)amino-1-(4'-methoxybenzyl)-1H-pyrazole; 4-amino-5-methylamino-1-(2'-hydroxyethyl)-1H-pyrazole; bis-(4,5-diaminopyrazole-1-yl)-methane; 1,2-bis-(4,5-diaminopyrazole-1-yl)-ethane; 1,3-bis-(4,5-diaminopyrazole-1-yl)-propane; 1,3-bis-(4,5-diamino-3-phenylpyrazole-1-yl)-propane; 2,3-bis-(4,5-diaminopyrazole-1-yl)-propane-1-ol; N-benzyl-2,3-bis-(4,5-diaminopyrazole-1-yl)-propionamide; 1,3-bis-(4,5-diaminopyrazole-1-yl)-cyclohexane; 1,4-bis-(4,5-diaminopyrazole-1-yl-methyl)-benzene; 1,4-bis-(4,5-diaminopyrazole-1-yl-methyl)-2,5-dimethoxybenzene; 1,3-bis-(4,5-diaminopyrazole-1-yl-methyl)-benzene; 2,6-bis-(4,5-diaminopyrazole-1-yl-methyl)-4-methylphenol; 1,2-bis-(4,5-diaminopyrazole-1-yl-methyl)-benzene; 1,2-bis-(4,5-diaminopyrazole-1-yl-methyl)-4,5-dimethoxybenzene; 2,3-bis-(4,5-diaminopyrazole-1-yl-methyl)-naphthalene; 2,3-bis-(4,5-diaminopyrazole-1-yl-methyl)-anthracene; 9,10-bis-(4,5-diaminopyrazole-1-yl-methyl)-anthracene; 4,4'-bis-(4,5-diaminopyrazole-1-yl-methyl)-biphenyl; 1,2-bis-[4-(4,5-diaminopyrazole-1-yl-methyl)-phenyl]-ethane; 2,5-bis-(4,5-diaminopyrazole-1-yl-methyl)-furan; 2,5-bis-(4,5-diaminopyrazole-1-yl-methyl)-thiophene; 2,8-bis-(4,5-diaminopyrazole-1-yl-methyl)-dibenzothiophene; 4,4'-bis-(4,5-diaminopyrazole-1-yl-methyl)-[2,2']bipyridyl and 1,2-bis-[6-(4,5-diaminopyrazole-1-yl-methyl)-pyridine-2-yl]-ethane; or is a salt thereof with an inorganic or organic acids.

3. The agent as defined in claim 1, wherein said at least one resorcinol derivative is 4-ethylresorcinol, 4-methylresorcinol, 2,4-dimethylresorcinol and/or 4-hexylresorcinol.

4. The agent as defined in claim 1, containing from 0.005 to 20 percent by weight of said at least one 4,5-diaminopyrazole derivative and from 0.005 to 20 percent by weight of said at least one resorcinot derivative.

5. The agent as defined in claim 1, further comprising oxidative dye precursors and/or substantive dyes.

6. The agent as defined in claim 5, wherein said oxidative dye precursors are developer substances and coupler substances.

7. The agent as defined in claim 6, containing from 0.01 to 20 percent by weight of said developer substances and from 0.01 to 20 percent by weight of coupler substances.

8. The agent as defined in claim 5, containing said substantive dyes in an amount of from 0.01 to 10 percent by weight.

9. A ready-for-use oxidation dye mixture having a pH of 3 to 11 and made by mixing the agent as defined in claim 1 with an oxidizing agent in a weight ratio of 5:1 to 1:3.

* * * * *